(12) United States Patent
Jensen et al.

(10) Patent No.: US 10,974,040 B2
(45) Date of Patent: *Apr. 13, 2021

(54) ELECTRODE ASSEMBLY HAVING VARIOUS COMMUNICATIVE SOLUTIONS

(71) Applicant: PHYSIO-CONTROL, INC., Redmond, WA (US)

(72) Inventors: Jennifer Goeman Jensen, Mill Creek, WA (US); Jennifer Elaine Hoss, Bothell, WA (US); Mitchell A. Smith, Sammamish, WA (US); Kenneth J Peterson, Bellevue, WA (US); Maren Louise Nelson, Kirkland, WA (US); Andres Belalcazar, Redmond, WA (US); Daniel W. Piraino, Seattle, WA (US); John Robert Knapinski, Kirkland, WA (US); Matthew L. Bielstein, Seattle, WA (US); Ethan P. Albright, Mill Creek, WA (US); Jeffery S. Edwards, Bellingham, WA (US); Paul S. Tamura, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 274 days.

This patent is subject to a terminal disclaimer.

(21) Appl. No.: 15/680,199

(22) Filed: Aug. 17, 2017

(65) Prior Publication Data

US 2017/0368328 A1 Dec. 28, 2017

Related U.S. Application Data

(63) Continuation of application No. 14/907,251, filed as application No. PCT/US2014/048300 on Jul. 25, 2014, now Pat. No. 9,844,658.

(60) Provisional application No. 61/971,488, filed on Mar. 27, 2014, provisional application No. 61/858,543, filed on Jul. 25, 2013.

(51) Int. Cl.
*A61N 1/04* (2006.01)

(52) U.S. Cl.
CPC .......... *A61N 1/046* (2013.01); *A61N 1/0492* (2013.01)

(58) Field of Classification Search
CPC .... A61N 2001/083; A61N 1/046; A61N 1/08; A61N 1/0492
See application file for complete search history.

(56) References Cited

U.S. PATENT DOCUMENTS

| | | |
|---|---|---|
| 6,075,369 A | 6/2000 | Morgan |
| 6,084,380 A | 7/2000 | Burton |
| 6,088,608 A | 7/2000 | Schulman et al. |
| 6,125,299 A | 9/2000 | Groenke et al. |
| 6,332,536 B2 | 12/2001 | Easton |
| 6,452,873 B1 | 9/2002 | Holt et al. |
| 6,560,485 B2 | 5/2003 | Herleikson |

(Continued)

OTHER PUBLICATIONS

International Search Report dated Dec. 11, 2014 for PCT/US2014/048300 dated Dec. 11, 2014.

(Continued)

*Primary Examiner* — Michael W Kahelin
(74) *Attorney, Agent, or Firm* — Lee & Hayes, P.C.

(57) ABSTRACT

Technologies and implementations for a defibrillator electrode having communicative capabilities are generally disclosed.

30 Claims, 8 Drawing Sheets

(56) References Cited

U.S. PATENT DOCUMENTS

| | | |
|---|---|---|
| 7,540,788 B2 | 6/2009 | Murphy et al. |
| 7,590,456 B2 | 9/2009 | Craige, III et al. |
| 8,086,306 B2 | 12/2011 | Katzman et al. |
| 8,330,932 B2 | 12/2012 | Mi et al. |
| 8,676,311 B2 | 3/2014 | Cordaro et al. |
| 2003/0231106 A1 | 12/2003 | Shafer |
| 2004/0162586 A1 | 8/2004 | Covey |
| 2005/0277991 A1* | 12/2005 | Covey ............... A61N 1/0492 607/5 |
| 2010/0023074 A1 | 1/2010 | Powers et al. |
| 2010/0220422 A1 | 9/2010 | Jackson |
| 2012/0197324 A1 | 8/2012 | Nova |
| 2013/0069679 A1* | 3/2013 | McIntyre ............ A61N 1/3931 324/750.3 |
| 2013/0244491 A1 | 9/2013 | Sarwar et al. |

OTHER PUBLICATIONS

International Preliminary Report on Patentability dated Jan. 26, 2016 for PCT/US2014/048300 dated Dec. 11, 2014.

Written Opinion dated Dec. 11, 2014 for PCT/US2014/048300 dated Dec. 11, 2014.

Examination Report dated Apr. 9, 2018, Australian patent application No. 2014292850.

The Australian Office Action dated Mar. 4, 2020 for Australian Application No. 2019204964, a counterpart foreign application of the U.S. Appl. No. 15/680,199, 4 pages.

International Preliminary Report on Patentability for PCT/US14/48300 dated Jan. 26, 2016, 9 pages.

International Search Report and Written Opinion for PCT/US14/48300 dated Dec. 11, 2014, 10 pages.

Extrended European Search Report dated May 29, 2020 for European Application No. 19217028.01, 7 pages.

\* cited by examiner

700 A computer program product

702 A signal bearing medium 704 at least one of machine readable non-transitory medium having stored therein instructions that, when executed by one or more processors, operatively enable a defibrillator electrode having communicative capabilities to:

detect an electrical signal at a defibrillator electrode;

determine an integrity level of a gel disposed on the defibrillator electrode, the determined integrity level having an indication of a conductivity level of the gel;

determine if the conductivity of the gel is within a predetermined range; and interrupt substantially most of the electrical signal between the defibrillator electrode and a defibrillator device.

| 706 a computer-readable medium | 708 a recordable medium | 710 a communications medium |

Figure 7

ELECTRODE ASSEMBLY HAVING VARIOUS COMMUNICATIVE SOLUTIONS

RELATED APPLICATION

This application claims benefit of priority to U.S. Provisional Patent Application Ser. No. 61/858,543, filed on Jul. 25, 2013, titled Smart Electrodes and to U.S. Provisional Patent Application Ser. No. 61/971,488, filed on Mar. 27, 2014, titled Smart Electrodes, both of which are incorporated herein by reference in their entirety.

BACKGROUND

Unless otherwise indicated herein, the approaches described in this section are not prior art to the claims in this application and are not admitted to be prior art by inclusion in this section.

A heart, such as a human heart, facilitates pumping of blood to and from various parts of a body. The heart commonly beats at a regular rate and regular rhythm. However, a symptom may occur, where the electrical control system of the heart may malfunction, which may cause the heart to beat irregularly or not at all. Additionally, the regular rhythm of the heart may be negatively affected, which may be generally referred to as an arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amount of blood or may not pump blood at all, which may eventually lead to death. Another type of arrhythmia, which may be associated with SCA, may be a condition known as ventricular tachycardia (VT). An electronic device may also be utilized to help sense, monitor, or treat a medical condition such as cardiac VF by defibrillating the heart. An example of an electronic device may be a defibrillator device. A defibrillator device may be capable of providing an electrical signal, commonly in the form of an electric shock, to the heart in the VF condition. The defibrillator device may provide the electrical signal to a heart externally (i.e., through the surface of a body) via accessories commonly known as electrodes. Commonly in the form of a pad, as the name may imply, the electrode may facilitate transfer of the electrical signal from the defibrillator device to the heart through the surface of the body. Because of the nature of the function of the electrode, the electrode may be considered to be a consumable accessory (i.e., the electrode may have a limited number of uses, may have a shelf life, may have compatibility requirements with certain defibrillator devices, etc.), albeit one of an important accessory.

SUMMARY

The present disclosure describes example methods, apparatus, and systems related to an electrode having communicative capabilities. Example apparatus may include a communicative apparatus for use with a defibrillator device. The communicative apparatus may comprise an electrode, where the electrode may be configured to be used with the defibrillator device, a thin film circuit disposed on a first surface of the electrode, where the thin film circuit may be configured to be a radio-frequency identification (RFID) circuit, a gel disposed on a second surface substantially opposite the first surface, a gel integrity sensor disposed in physical contact with the gel, where the gel integrity sensor may be communicatively coupled to the thin film circuit, and a connector electrically coupled to the electrode, where the connector may be configured to electrically connect the electrode to the defibrillator device and be communicatively coupled to the thin film circuit.

Another example apparatus may include a communicative apparatus for use with a defibrillator device. The communicative apparatus may comprise an electrode, a watermark, where the watermark may be integrated with the electrode on a first surface of the electrode, a gel, where the gel may be disposed on a second surface substantially opposite the first surface of the electrode, a connector, where the connector may be electrically coupled to the electrode, where the connector may be configured to electrically connect the electrode to the defibrillator device, and an electrical signal interrupt module communicatively coupled to the connector and the defibrillator device, where the electrical signal interrupt module may be configured to interrupt an electrical signal from the defibrillator device based, at least in part, on an interrupt signal from the defibrillator device.

Another example apparatus may include a communicative apparatus for use with a defibrillator device. The communicative apparatus may comprise of an electrode, a printed circuit disposed on a first surface of the electrode, a display device disposed on the first surface of the electrode, where the display device may be communicatively coupled to the printed circuit, a gel disposed on a second surface substantially opposite the first surface, a gel integrity sensor disposed in physical contact with the gel, where the gel integrity sensor may be communicatively coupled to the printed circuit, a connector electrically coupled to the electrode, where the connector may be configured to electrically connect the electrode to the defibrillator device, and an electrical signal interrupt module communicatively coupled to the connector and the defibrillator device, where the electrical signal interrupt module configured to interrupt an electrical signal from the defibrillator device based, at least in part, on an interrupt signal from the printed circuit.

Another example apparatus may include a communicative apparatus for use with a defibrillator device. The communicative apparatus may comprise of an electrode, where the electrode may be configured to be used with the defibrillator device, a thin film circuit disposed on a surface of the electrode, the thin film circuit may be configured to be a storage medium, and a connector electrically coupled to the electrode, where the connector may be configured to electrically connect the electrode to the defibrillator device and be communicatively coupled to the thin film circuit.

An example method may include detecting an electrical signal at a defibrillator electrode, determining an integrity level of a gel disposed on the defibrillator electrode, where the determined integrity level may have an indication of a conductivity level of the gel, determining if the conductivity of the gel is within a predetermined range, and interrupting substantially most of the electrical signal between the defibrillator electrode and a defibrillator device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 7 illustrates an example computer program product 700, arranged in accordance with at least some embodiments described herein.

DETAILED DESCRIPTION

Figure 1:
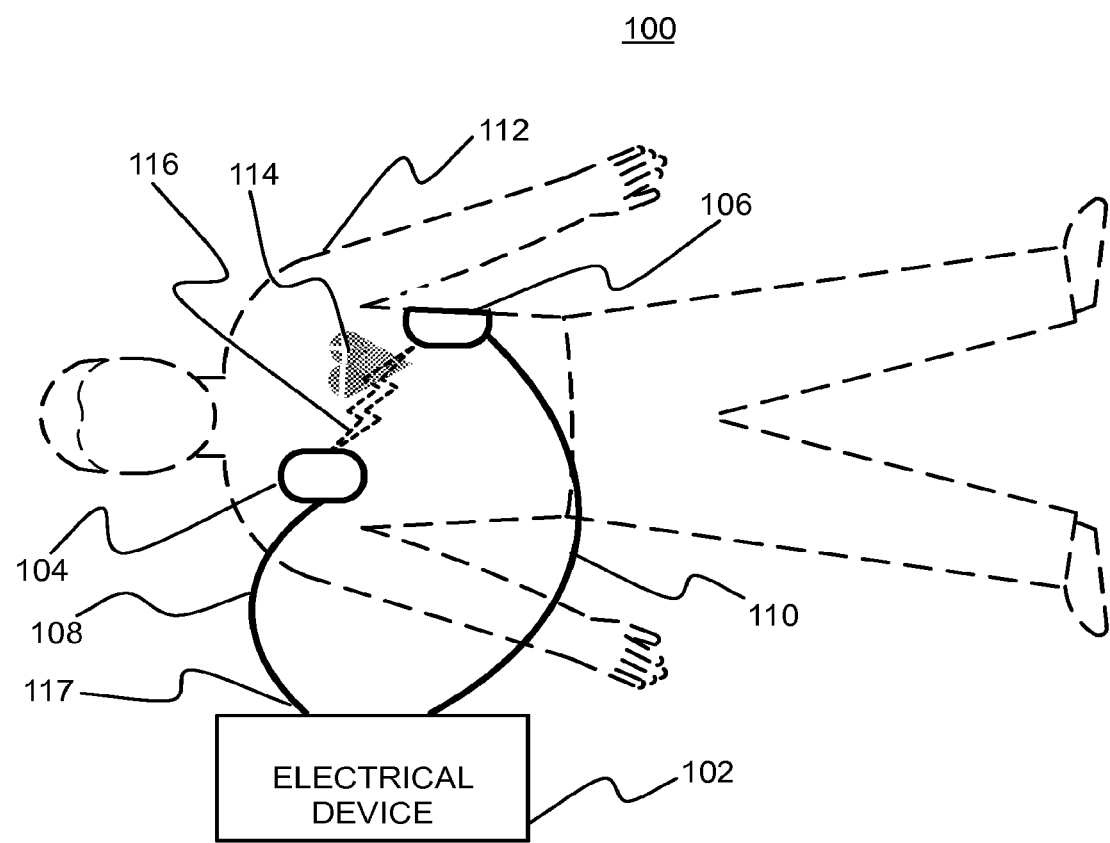
FIG. 1 illustrates an example system for use with a communicative apparatus, in accordance with various embodiments.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to an electrode, which may also be referred to as electrode assembly or electrode package. Such electrode may include electrode pads also known as communicative apparatuses, signal lines, and/or a connector, which may facilitate interfacing with an electrical device, such as, but not limited to, a medical device (e.g., a defibrillator type device) and having various communicative capabilities.

Heart related issues have become prevalent throughout many parts of the World. For example, in the United States, coronary heart disease may be considered a health problem. Coronary heart disease may lead to issues related to the heart such as, but not limited to, arrhythmia. Some arrhythmias may lead to a condition known as sudden cardiac arrest (SCA). An example condition of SCA may be ventricular fibrillation (VF), where the heart muscles may basically quiver and not pump blood. Such conditions may be detected, monitored, and treated utilizing electrical devices and their respective accessories, where the accessories may include electrical accessories such as, but not limited to, electrodes. These electrodes may be utilized as therapy and/or monitoring electrodes and may include metallic plate separated by a dielectric type of material.

In order to treat a heart in a condition of VF, the heart may need to be defibrillated by the application of an electrical signal (e.g., an electric shock). In order to defibrillate the heart, a medical device such as a defibrillator device may be utilized. A defibrillator device may facilitate administration of an electrical shock to the heart, thereby defibrillating the heart undergoing VF. The shock may terminate VF providing the heart the opportunity to resume pumping blood. If VF is not terminated, the shock may be repeated at varying energies or VF may lead to the death of the person.

A challenge with defibrillation may be that the electrical shock should be administered very soon after the onset of VF. The challenge of defibrillating early after the onset of VF may be met in a number of ways. For example, a person who may be considered to be at a high risk of VF or other heart arrhythmia may have an Implantable Cardioverter Defibrillator (ICD). An ICD may monitor the person's heart and administer an electrical signal as needed. As such, an ICD may reduce the need to have the high-risk person be monitored constantly by medical personnel. In some instances, a person may be diagnosed as being at risk, but must wait for an ICD. In such instances, the person may be monitored with a wearable device or a device, which a person may be able to carry. The wearable device (not shown) may include monitoring electrodes. Based, at least in part, on the condition of the person wearing a wearable device, the device and/or the electrodes may be capable of calling for help and/or discharging a shock using therapy electrodes. In the meantime, an alarm may be transmitted and help may be on the way with emergency equipment. Such types of electrodes may then be disconnected from the wearable device and re-plugged into another device, such as the device brought to the scene by an emergency/medical personnel or any one else.

Unfortunately, in some instances, VF may occur unpredictably to any person, even to a person who may not have been considered to be at high risk. When VF occurs to a person who does not have an ICD, the person may collapse due to inadequate and/or lack of blood flow. The person undergoing VF should receive treatment including defibrillation as quickly as possible and easy transferability of connectors, devices and/or data may facilitate saving of time and/or potentially, life of a person.

For a person experiencing VF without an ICD, an external type of defibrillator device may be utilized to defibrillate the heart. There may be several types of external defibrillator devices such as, but not limited to, wearable defibrillators, manual defibrillators, semi-automated defibrillators, and automated defibrillators. An example type of external defibrillator device may include defibrillator devices intended to treat multiple people using disposable electrodes and/or more permanent electrodes (e.g., paddles). The defibrillator devices found in medical centers may be described as advanced life support (ALS) type defibrillator devices. ALS type defibrillator devices may have a wide range of functionalities including allowing healthcare professionals to monitor a person's rhythm via electrodes and manually intervene if is determined that a shock is necessary.

Another example type of external defibrillator device may include a defibrillator device intended to treat a limited number of people such as, but not limited to, a single person. Single person type external defibrillators may include relatively small (i.e., portable) external defibrillator devices. An example of a single person type external defibrillator may be an automated external defibrillator (AED) type device. AED type devices may be found in various private and/or public places such as, but not limited to, offices, train stations, airports, stadiums, hospitals, homes, vehicles, vessels, planes, trains, automobile, etc. AED type devices may be commonly for use by a layperson and/or a person with basic life support training.

Another example type of external defibrillator device may include wearable defibrillator devices, which may be worn outside the body. Wearable defibrillator devices may continuously monitor a person's heart with electrodes capable of sensing to detect VF or other heart arrhythmia. Wearable defibrillator devices may provide an intermediate care option for a person having a high risk of a coronary heart event and/or a person who may not be a candidate for an ICD.

Since the electrical device may be used to treat a person, to help ensure proper operation, each type of a defibrillator/monitor may be designed to be compatible with proper fitting, and up-to-date electrodes, which may be encrypted for device recognition and/or adjustment of functionality based, at least in part, on an encryption pairing and/or authentication.

For the purposes of describing the disclosed subject matter, references may be made to AED type devices. However, it should be appreciated that AED type devices are but one non-limiting example, and accordingly, in this respect, the claimed subject matter is not limited.

Continuing with the non-limiting example of an AED type device, a common AED type device may be have a form factor similar to a small portable carry case and may include a handle. Commonly, an AED type device may include a power source (e.g., a battery), a processor (e.g., computing/control module), and at least two electrodes (e.g., electrode pads). Additionally, an AED type device may be of at least two types, semi-automated and fully automated defibrillators.

Defibrillator type devices may have various accessories. One example of an accessory, which may be commonly used with defibrillator type devices, may be electrodes. In the non-limiting example of an AED, an AED may have two electrodes communicatively coupled to it. Alternatively, an AED may have a single electrode having capabilities of communicating an electrical signal to and from the heart (e.g., a large butterfly shaped single electrode pad having two contacts). As part of a non-limiting example, usage of a defibrillator may be described.

In an example scenario, a person may be undergoing VF and may be on the ground in a public space (e.g., a subway station). A user may see the person and locate and retrieve an AED from its holding location (e.g., AED cabinet on a column and/or wall). The user would open the AED package and proceed to turn on the AED, at which point, the AED will instruct the user to attach the electrodes to the person. Alternatively, the user may turn on the AED and proceed to open the electrode assembly/package. However, the process by which the user may proceed to utilize the AED may be in a wide variety of manners based, at least in part, on the manufacturer of the AED and/or the electrode and/or the applicability of the AED. The electrodes may be in individual packages to be opened and connected to the AED before being placed on the person.

It should be appreciated that in some implementations, the electrodes may already be connected to the defibrillator type device. For example, the defibrillator device may be a type of device utilized by emergency personnel (i.e., as a person is being transported or at a medical facility).

The electrodes may be placed on a person undergoing VF at appropriate locations on the person's body, as instructed by the AED. Appropriate placement of the electrodes may effectively provide the electrical shock to the person's heart. Once the electrode pads are placed in the appropriate locations on the person's body, the electrodes may provide an electrical signal to the AED, where the processor may determine the rhythm of the heart (i.e., the AED may read electrical signals from the electrodes). Once the rhythm of the heart is determined, the processor of the AED may control the AED to charge itself to an appropriate level and indicate to the user of the AED that the person undergoing VF will need to be electrically shocked. At this point, in the case of an automated AED, the AED may provide various warnings to the user of the AED and/or to anyone else in the vicinity of the AED and proceed to administer the electrical shock to the person undergoing VF. Alternatively, in the case of a semi-automated AED, the user of the AED may be provided an indication (e.g., audio and/or visual signal) by the AED to activate the electrical shock (e.g., by pressing a button on the AED). In either scenario, a good outcome would be that the person undergoing VF may be defibrillated by the electrical shock.

As described above, because defibrillation includes electrical signals (e.g., either heart rhythm information to the AED and/or electrical shock to the person undergoing VF), proper contact between the electrodes and the person may provide the desired electrical connectivity between the electrode pads and the person to deliver the appropriate electrical shock. In order to help facilitate proper contact between an electrode and a person, the electrode pads may have a gelatin like substance. The gelatin like substance may be of the type that may provide sufficient contact with the skin of a person to facilitate proper electrical signals to and from the person. The gelatin like substance (here on out "gel") may be a wide variety of aqueous solutions such as, but not limited to, gels having low electrical impedance. A gel may provide not only proper contact with the skin of the person, but may also facilitate proper adhesion with the skin of the person. Two examples of gels may be a wet gel and a solid gel, where the wet gel may be more aqueous, while the solid gel may be more solid than aqueous. A wide variety of dielectric type materials may also be utilized.

It may be noted here that in order to facilitate proper type of defibrillation by an AED, the AED should be able to receive electrical signals from the person undergoing the arrhythmia. Accordingly, proper contact with the person's skin may be important in order for the AED to receive the appropriate electrical signals to properly treat the person (e.g., deliver the correct amount of shock and at the appropriate time). In order to facilitate proper contact with a person's skin, a gel may be applied to the electrode pads. The gel may be utilized as a bonding material between the electrodes and the skin of the person (e.g., by the gel seeping into the pores of the person). However, over time and/or due to incorrect storing conditions, such as high temperature, for example, the gel may deteriorate and the electrode pad's electrical properties may be compromised (e.g., may dry out, lose its effectiveness, and/or chemically breakdown). In order to address potential integrity issues with the gel, a common method by a manufacturer of an electrode may be to provide an expiration date, beyond which the gel may lose its effectiveness. For example, the gel may not adhere properly to the skin of a person, and may result in the electrode not maintaining proper contact with the person's skin (e.g., perhaps during movement of the skin under cardio pulmonary resuscitation or CPR compressions). Thus, the integrity of the gel may be considered to be one of many important factors for improving the chances of survival for a person undergoing some form of heart arrhythmia.

Either a defibrillator device manufacturer may typically produce accessories, such as electrodes, or a company authorized by the defibrillator device manufacturer. These accessories may be made to various standards to work properly with the defibrillator device. While transferability of accessories may be important time saving feature, some companies may make accessories that may not necessarily be authorized by the device manufacturer but still may work with the defibrillator device (e.g., aftermarket as opposed to original equipment manufacturer or OEM). These accessories may be known as unauthorized accessories. At times, unauthorized accessories may not be made to the quality standards as prescribed by certain defibrillator device manufacturers (i.e., authorized accessories) or may not be fully verified with certain defibrillators. For example, unauthorized accessories may not have been tested or validated with the device to confirm functionality, and accordingly, their efficacy may not be able to be confirmed to ensure that the overall system may function as intended (i.e., to potentially address a life threatening situation). As a result, some unauthorized accessories may cause the defibrillator device to not function as well, or even may cause the defibrillator device to malfunction, including person not being defibrillated properly and/or not receiving the necessary shock or shock level, both of which may compromise the proper treatment of a person, which may ultimately even lead to death of the person (i.e., a potential safety issue). Users may not necessarily be able to distinguish between authorized and unauthorized accessories because some unauthorized accessories may be produced and marked similarly to authorized accessories. Thus, is may be difficult to determine whether the accessory is an authorized accessory or an unauthorized accessory (i.e., chance that the accessory will operate properly). As such, electrodes as disclosed herein may include security features such as, but not limited to, encryption key or encryption data. For example, when communicatively coupled with an electronic device (e.g., plugged into a device), the electrodes may be identified by the device and/or recognizable by the device, and accordingly, may facilitate transfer of electrode and/or person information (e.g., electrode and/or patient data) to any other device.

Before moving on to the description of the figure, even though the above may have been mostly described with respect to a defibrillator device, it should be appreciated that it is contemplated within the present disclosure that the claimed subject matter may be applicable to a wide variety of devices, which may or may not utilize electrode type devices, such as, but not limited to, biosensor type devices. In one example, a biosensor type device may monitor electrical activity of a person by monitoring the electrical activity of the person's heart over time such as, but not limited to, electrocardiogram (i.e., ECG or EKG). In another example, an electrode or electrodes may be utilized by a biosensor device, which may monitor cerebral activity (i.e., electroencephalography as may be monitored by an EEC biosensor device). Accordingly, the claimed subject matter is not limited in scope to the particular implementations described herein.

Additionally, it should be appreciated that a person may include the young and the elderly. Accordingly, it is contemplated within the present disclosure that the claimed subject matter may be applicable to a wide variety persons such as, but not limited to, children (i.e., pediatric), elderly (i.e., geriatric), male, female, and so forth. For example, an electrode and/or electrical device may have the capabilities to determine whether to administer and/or treat a pediatric person or a geriatric person, and any range in between. Accordingly, the claimed subject matter is not limited in scope to the particular implementations described herein.

Because the disclosure encompasses a wide variety of devices, it is contemplated within the present disclosure that the claimed subject matter is not limited to devices, which may use electrodes. For example an electrode may be able to communicate and/or provide information to a wide variety of devices, including those devices that may not necessarily utilize electrode type devices. In one example, an electrode type device may include information about a first device the electrode device may have been attached and utilized, and subsequently, the electrode type device may provide the information about the first device to a second device. The information may include any information such as, but not limited to storage device identification number, electrode type device lot number, electrode type device date of manufacture, electrode type device expiration date, electrode type device date installed, electrode type device manufacturer part number, electrode type device lot code, use-by date, date of manufacture of the electrode type device, functionality of the electrode type device, cyclic redundancy check (CRC) of the electrode type device, serial number for the first device the electrode type device was installed, date of installation for the first device, serial number of the second device the electrode type device was installed, date of installation for the second device, so forth, number of shocks delivered with the electrode type device, minutes of monitoring with electrode type device, minutes of pacing with the electrode type device, time worn with the electrode type device, maximum number of uses (if reusable) with the electrode type device, etc. In another example, an electrode type device may have been first attached to an AED, and then communicatively coupled to a subsequent medical device, which may have capabilities of analyzing all, any, and any combination of information from the electrode type device. Accordingly, the claimed subject matter is not limited in scope to the particular implementations described herein.

FIG. 1 illustrates an example system for use with a communicative apparatus, in accordance with various embodiments. Shown in FIG. 1, a system 100 may comprise an electrical device, such as, but not limited to, a defibrillator device 102, a first communicative apparatus 104, and a second communicative apparatus 106. The first communicative apparatus 104 and the second communicative apparatus 106 may be communicatively coupled to the defibrillator device via a first signal line 108 between the first communicative apparatus 104 and the defibrillator device 102 and a second signal line 110 between the second communicative apparatus 106 and the defibrillator device 102. Additionally, an outline of a person 112 may be illustrated to provide an example context to the disclosed subject matter. A representation of a human heart 114 may also be illustrated in FIG. 1. As will be described in detail, the system 100 may facilitate utilization of a defibrillator electrode having various communicative capabilities, in accordance with various embodiments.

The first communicative apparatus 104 and the second communicative apparatus 106 may comprise of electrodes configured for use with the defibrillator device 102, and accordingly, the first communicative apparatus 104 and the second communicative apparatus 106 may be collectively referred to as an electrode or an electrode pad. Additionally, it should be appreciated that even though two communicative apparatuses 104 and 106 may be shown in FIG. 1, two communicative apparatuses 104 and 106 may be a single communicative apparatus (e.g., a single pad having contacts to provide electrical signaling across the heart 114). Accordingly, for ease of understanding the disclosure, the first communicative apparatus 104 and the second communicative apparatus 106 together with a first signal line 108 between the first communicative apparatus 104 and the defibrillator device 102 and a second signal line 110 between the second communicative apparatus 106 and the defibrillator and the connector 117 connecting the first communicative apparatus 106 and second communicative apparatus 108 via the signal lines to the defibrillator device 102 may be referred to collectively as an electrode, electrode assembly, electrode package, and so forth. However, for the ease of understanding and describing the disclosure, the two communicative apparatuses 104 and 106 may be referred to as electrodes. As illustrated in FIG. 1, an electrical signal 116 may pass between the electrodes 104 and 106, which may cause defibrillation of the heart 114. As will be described in further detail, the electrodes 104 and/or 106 may have various communicative capabilities, in accordance with various embodiments. As part of the communicative capabilities, it is contemplated within the scope of the claimed subject matter that the communicative capabilities may include a wide variety of communicative capabilities such as, but not limited to, wired, wireless, infrared communication, near field communication (NFC), Bluetooth, WiFi (any implementation of wireless protocols, e.g., 802.11), and/or any combination thereof. Accordingly, the claimed subject matter is not limited in scope to the particular implementations described herein.

Figure 2A:
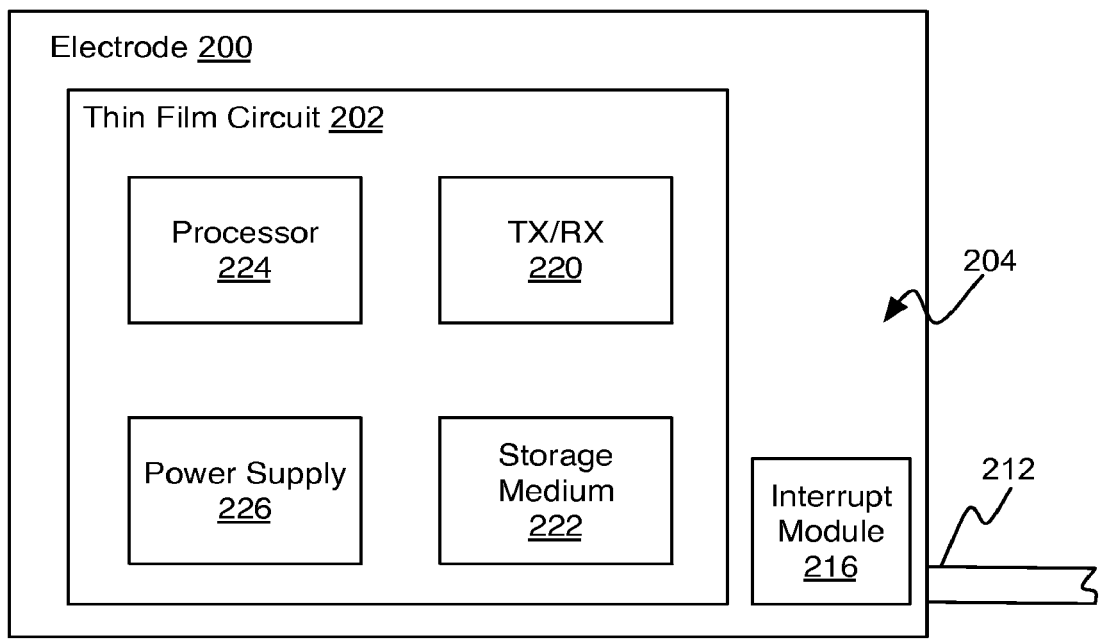
FIGS. 2a and 2b illustrate block diagrams of an electrode having communicative capabilities, in accordance with various embodiments.
Figure 2B:
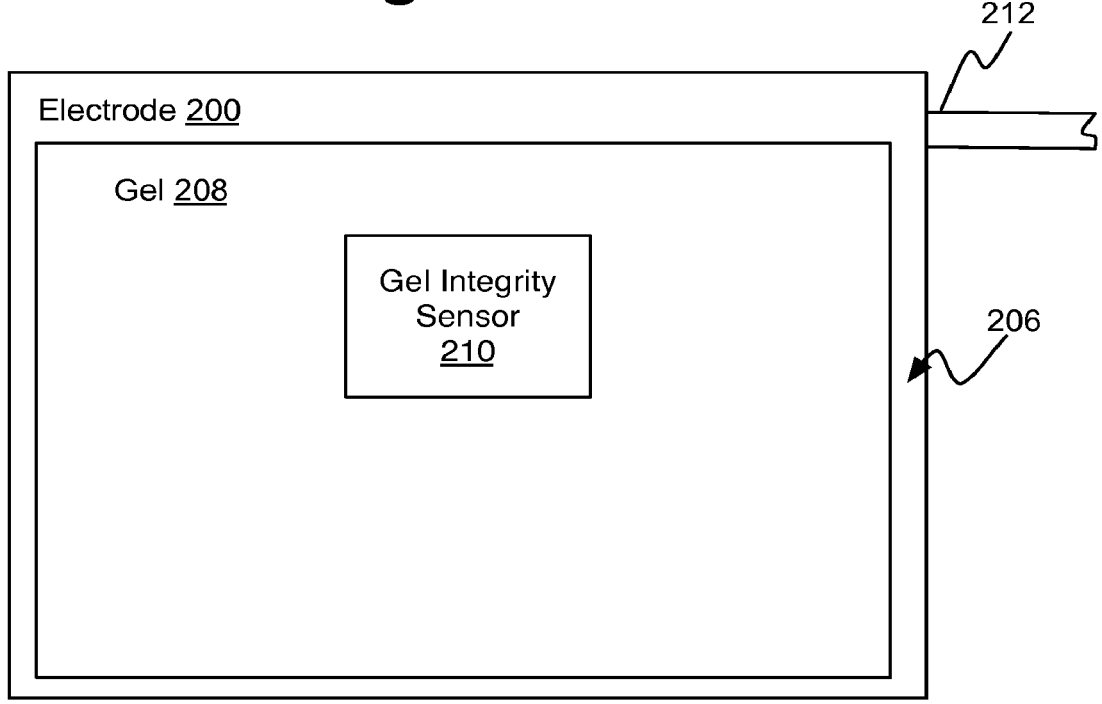

FIGS. 2a and 2b illustrate block diagrams of an electrode having communicative capabilities, in accordance with various embodiments. Shown in FIG. 2a is an electrode 200, which may be configured to be used with a defibrillator device 102. The electrode 200 may have a thin film circuit 202 disposed on a first surface 204 of the electrode 200. The thin film circuit 202 may include various functional blocks such as, but not required or limited to, a transmit and/or receive module 220, a storage medium 222, a processor module 224, and a power supply module 226. Alternatively, a storage medium 222, and/or a processor module 224, and/or a power supply module 225 may be included with the connector 212. In still further examples, no processor module 224 may be included.

In one example, the thin film circuit 202 may be configured to be a radio-frequency identification (RFID) circuit. In another example, the thin film circuit 202 may be configured to be an RFID tag, and further be configured to be at least one of a passive RFID tag, an active RFID tag, or a battery-assisted RFID tag.

In FIG. 2b, a second surface 206 of the electrode 200 may be shown. The second surface 206 may be substantially opposite the first surface 204 (shown in FIG. 2a), and a gel 208 may be disposed on the second surface 206. Additionally, a gel integrity sensor 210 may be disposed in physical contact with the gel 208. The gel integrity sensor 210 may be communicatively coupled to the thin film circuit 202. In both FIGS. 2a and 2b, a connector 212 may be shown electrically coupled to the electrode 200 and configured to electrically connect the electrode 200 to the defibrillator device 102. In some examples, the connector 212 may be transferable, where the connector 212 is capable of being disconnected from one type of a device and connected to another electrical device. For example, the connector 212 may be disconnected from a wearable and/or a monitoring device to a defibrillator type device or another electrical device brought in by en emergency/medical personnel or a bystander in some situations. The connector 212, may then facilitate efficient information (i.e., data) transfer with respect to a person and/or an electrical device the connector 212 was previously communicatively between devices and/or computing devices/systems. For example, devices manufactured by the same manufacturer. Using the same connector 212, a patient monitoring module may be paired with an electrical device such as, but not limited to, a defibrillator type device, without the need to disconnect the electrodes from either the person and/or the person monitoring device/module. In another example, the electrode 200 may not need to be disconnected from the person, but however, if another defibrillator type device is utilized, the connector 212 may be re-attached to another electrical device. In such an example, the electrode 200 may facilitate transfer of the monitoring and/or therapy information along with a wide range of information regarding the person and/or the electrode 200 to the other electrical device, such as, but not limited to, a defibrillator, a computer, a biosensor, and so forth.

The electrode 200 shown in FIGS. 2a and 2b may facilitate various communicative capabilities for use with the defibrillator device 102, in accordance with at least some embodiments.

In one example, the gel integrity sensor 210 may be a conductivity sensor capable of determining a conductivity level of the gel 208. Additionally, the gel integrity sensor 210 may be capable of communicating the determined conductivity level of the gel 208 to the thin film circuit 202. In another example, the gel integrity sensor 210 may be a combined humidity and temperature sensor. In this example, the gel integrity sensor 210 may be capable of determining the humidity and temperature the gel 208 may have been subjected to before being communicatively coupled to the defibrillator device 102.

The gel 208 may be an aqueous material, which may be at least one of a conductive gel and/or an adhesive gel for use with the electrode 200 (e.g., an electrolytic gel). Additionally, the gel 208 may be disposed on the second surface 206 in a package form (e.g., a packaged gel having adhesive properties on a surface for contact with the body of a person).

The connector 212 may include an electrical signal interrupt module 216 communicatively coupled to the thin-film circuit 202. In the example of the connector 212 including the electrical signal interrupt module 216, the connector 212 may be configured to interrupt substantially most electrical signals between the electrode 200 and the defibrillator device upon receiving an interrupt signal from the thin film circuit 202. As will be described, not all electrical signals may be interrupted, but at least the electrical shock may be interrupted.

Shown in FIG. 2a is a connector 212, which may be configured to be used with an electrical device such as, but not limited to, the defibrillator device 102 (shown in FIG. 1). In should be appreciated that in some examples, the connector 212 may include various functional blocks such as, but not required or limited to, a transmit and/or receive module, such as module 220, a storage medium such as storage medium 222, a processor module such as processor module 224, and a power supply module, such as power supply module 226. Alternatively, a storage medium 222, and/or a processor module 224, and/or a power supply module 225 may not be included with the connector 212. By way of an example, the connector 212 may include and implement various security features such as, but not limited to, encrypted identification information to facilitate recognition and utilization of the connector 212 and/or electrode 200 by an electronic device, where the security features may be implemented by a particular manufacturer and may adjust its levels of functionality based, at least in part, on the electrical device the connector 212 and/or the electrode 200 as being paired with and/or communicatively coupled to.

A non-limiting example of utilization of the electrode 200 may now be described. Referring back to FIG. 1, the first communicative apparatus 104 and the second communicative apparatus 106 may comprise of the electrode 200 described in FIGS. 2a and 2b. For this non-limiting example, references may be made to the electrode 200 to describe the various functionalities of the first communicative apparatus 104 and the second communicative apparatus 106. Continuing to refer to FIG. 1, a user (not shown) may have seen a person 112 experiencing some form of heart event such as, but not limited to, an arrhythmia event (e.g., VF). The user may have located and retrieved a defibrillator device 102 (e.g., an AED type device) from its holding location (e.g., AED cabinet on a column and/or wall not shown). The user would open the defibrillator device package (not shown) and proceed to turn on the defibrillator device 102.

Referring now to FIGS. 2a and 2b, in one example, once the defibrillator device 102 is turned on, an electrical signal may be wirelessly broadcast from the defibrillator device 102. The electrical signal from the defibrillator device may be in the form of an electromagnetic (EM) signal. The electrode 200 may receive the EM signal and respond to the EM signal. For example, the EM signal may be received by the thin film circuit 202 via the transmit and/or receive module 220, and the received EM signal may be utilized by the power supply 226 to supply power to the processor 224. The processor 224 may read instructions from the storage medium 222. In one example, the instructions from the storage medium 222 may include instructions that, when executed by the processor 224, causes the processor 224 to determine the integrity of the gel 208 on the second surface 206. The integrity of the gel may be determined by data received from the gel integrity sensor 210 by the processor 224. The gel integrity sensor 210 may be capable of measuring the conductivity level of the gel 208. The processor 224 may receive the conductivity information from the gel integrity sensor 210. The processor 224 may determine if the received conductivity level is within a predetermined range (e.g., impedance levels) as may be stored in the storage medium 222.

In one example, if the processor 224 determines that the impedance level of the gel 208 is outside a predetermined level and/or the impedance to determine if the electrodes are properly operational and/or properly communicatively coupled to the defibrillator device and to the person 112, the processor 224 may cause an interruption of substantially most of the electrical signals between the electrode 200 and the defibrillator device 102 via the electrical signal interrupt module 216 (e.g., voltage for the shock 116, while allowing electrical signals related to the heart 114 to continue being transmitted to the defibrillator device 102). In another example, the processor 224 may store the determined conductivity level of the gel in the storage medium 222 along with information such as, but not limited to, humidity and/or temperature information of the gel 208. Additionally, the processor 224 may execute instructions that cause the electrode 200 to transmit via a wireless signal to the defibrillator device 102 various information stored in the storage medium 222 such as, but not limited to, the conductivity level of the gel 208, serial number and/or identification of the electrode 200, date of manufacture of the electrode 200, an expiration date of the electrode 200, an defibrillator device compatibility information (i.e., manufacturer compatibility with the electrode 200), number of cycles the electrode 200 has been subjected to, electrical capabilities of the electrode 200, maximum recommended number of uses for the electrode 200, identification of different devices to which the electrode 200 may have been previously connected, time the electrode 200 has been attached to a person, and so forth. Alternatively, the electrode 200 may transmit any and/or all of the mentioned information via the connector 212 to the defibrillator device 102. In turn, the defibrillator device 102 may cause an interruption of substantially most of the electrical signals between the electrode 200 and the defibrillator device 102 via the electrical signal interrupt module 216 (e.g., voltage for the shock, while allowing electrical signals related to the heart 114 to continue being transmitted to the defibrillator device 102). If the defibrillator device 102 causes an interruption of substantially most of the electrical signal, the defibrillator device 102 may further instruct the user to connect alternate electrodes, which may be included with the defibrillator device 102.

Referring back to FIG. 1, a defibrillator device 102 may be shown. However, it should be appreciated that it is contemplated that the defibrillator device 102 may be any type of defibrillator device as previously mentioned, such as, but not limited to, wearable defibrillators, manual defibrillators, semi-automated defibrillators, and automated defibrillators. Accordingly, the claimed subject matter is not limited in scope to the particular implementations described herein. Additionally, in FIG. 1, the first communicative apparatus 104 and the second communicative apparatus 106 may be shown as disposed on the person 112 in positions on the body of the person 112, which may be common to adults. However, it should be appreciated that the positions of the first communicative apparatus 104 and the second communicative apparatus 106 may vary such as, but not limited to, a first communicative apparatus disposed on the front of the person 112 and a second communicative apparatus disposed on the back of the person 112 (e.g., in the case of a small child, where the positions shown in FIG. 1 may be difficult to achieve). Additionally, as previously described, the first communicative apparatus 104 and the second communicative apparatus 106 may be integrated as a single apparatus (e.g., a single pad having a butterfly type configuration with electrical contacts/electrodes on either "wing" of the pad). Accordingly, the claimed subject matter is not limited in scope to the particular implementations described herein.

In FIGS. 2a and 2b, it should be appreciated that in order to provide a clear understanding of the disclosed subject matter, the various components and/or implementations are shown as block diagrams. For example, the electrode 200 may have a wide variety of shapes and sizes such as, but not limited to, substantially circular, substantially rectangular, etc., and accordingly, the claimed subject matter is not limited in scope to the particular implementations described herein. Additionally, it should be appreciated that the thin film circuit 202 may be implemented in a wide variety of manners. As previously mentioned, in one example, the thin film circuit 202 may be configured to be an RFID circuit. In this example, the thin film circuit 202 may be configured to be at least one of a passive RFID tag or an active RFID tag. In the example of a passive RFID tag, the passive RFID tag may not have an active power source, but instead, may generate energy from the EM signal emitted by a reader (e.g., defibrillator device 102) and may wirelessly communicate with the defibrillator device by changing the electrical loading/impedance (e.g., backscatter a signal). The power supply 226 may be in the form of a capacitor to facilitate charging by the EM signal, and thereby providing power to the thin film circuit 202. In the example of an active RFID tag, the active RFID tag may have an active power source and may wirelessly communicate with a reader (e.g., defibrillator device 102) via an Ultra-High Frequency (UHF) wireless signal. Accordingly, the claimed subject matter is not limited in scope to the particular implementations described herein.

The storage medium 222 of electrode 200, either the pads or the connector, or both may include a wide variety of memory type devices such as, but not limited to, RAM, ROM, EEPROM, flash memory or other memory technology, and accordingly, in this respect, the claimed subject matter is not limited in scope. The processor 224 may include a wide variety of processors such as, but not limited to, a microprocessor (µP), a microcontroller (µC), a digital signal processor (DSP), or any combination thereof. Processor 224 may include one or more levels of caching, such as a level one cache and a level two cache, a processor core, and registers. A memory controller may also be used with the processor 224, or in some implementations the memory controller may be an internal part of the processor 224, and accordingly, claimed subject matter is not limited in scope to the particular implementations described herein.

Additionally, in some example implementations, based, at least in part, on the desired functionality and/or implementations, the electrode 200 may include some, while not others, of the various components. For example, the electrode 200 may include the storage medium 222 while not the processor 224, while in other implementations, the electrode 200 may include the storage medium 222 while not the processor 224 or the transmit and/or receive module 220, or any combination/substitution thereof. Accordingly, in at least this respect, the claimed subject matter is not limited in scope.

In FIG. 2b, as previously described, the gel integrity sensor 210 may include sensors and/or combined digital humidity and temperature sensors. Other sensors may also be utilized. The conductivity sensors may include a wide variety of conductivity sensors such as, but not limited to, thin film conductivity sensors. The combined digital humidity and temperature sensors may include a wide variety of humidity and temperature sensors such as, but not limited to, thin film combined digital humidity and temperature modules. Briefly referring back to FIG. 1, in another example, a capacitance across the first communicative apparatus 104 and the second communicative apparatus 106 may be detected and/or measured. A defibrillation port, as will be described in detail later, may facilitate the detection and/or measurement of the capacitance across the first communicative apparatus 104 and the second communicative apparatus 106. In this non-limiting example, if the detected and/or measured capacitance is relatively low, the relatively low capacitance may be an indication of the electrical system as a whole (e.g., the first signal line 108 between the first communicative apparatus 104 and the defibrillator device 102, the second signal line 110 between the second communicative apparatus 106 and the defibrillator device 102, so forth, and/or any combination thereof) having an electrical issue such as, but not limited to a disconnect some place. However, if the detected and/or measured capacitance is relatively intermediate, the relatively intermediate capacitance may be an indication of the first communicative apparatus 104 and the second communicative apparatus 106 being properly electrically communicatively coupled, but may be an indication of the integrity of the gel 208 being negatively affected (e.g., may be dry). If there is an indication of the integrity of the gel 208 being negatively affected, the gel integrity sensor 210 may be configured to be a thermistor type device to measure the temperature of the gel 208. Further, if the detected and/or measured capacitance is relatively high (e.g., approximately at or above 80 picofarad), the relatively high capacitance may be an indication of the electrical system as a whole being in proper electrical condition.

Continuing with the non-limiting example of detecting and/or measuring capacitance, in one example, the first communicative apparatus 104 and the second communicative apparatus 106 may include a metallic foil type backing to relatively increase the capacitance and/or may improve a signal to noise ratio of the electrical system as a whole. For this example, a relative difference between an electrical system having potential electrical issues with an electrical system not having potential electrical issues may be higher (e.g., approximately 250 picofarad). As previously described, the gel integrity sensor 210 may indicate a relatively low humidity, which in turn, may indicate low moisture content in the gel 208, thereby may be an indication of not optimum gel quality. Accordingly, in at least this respect, the claimed subject matter is not limited in scope.

Figure 3A:
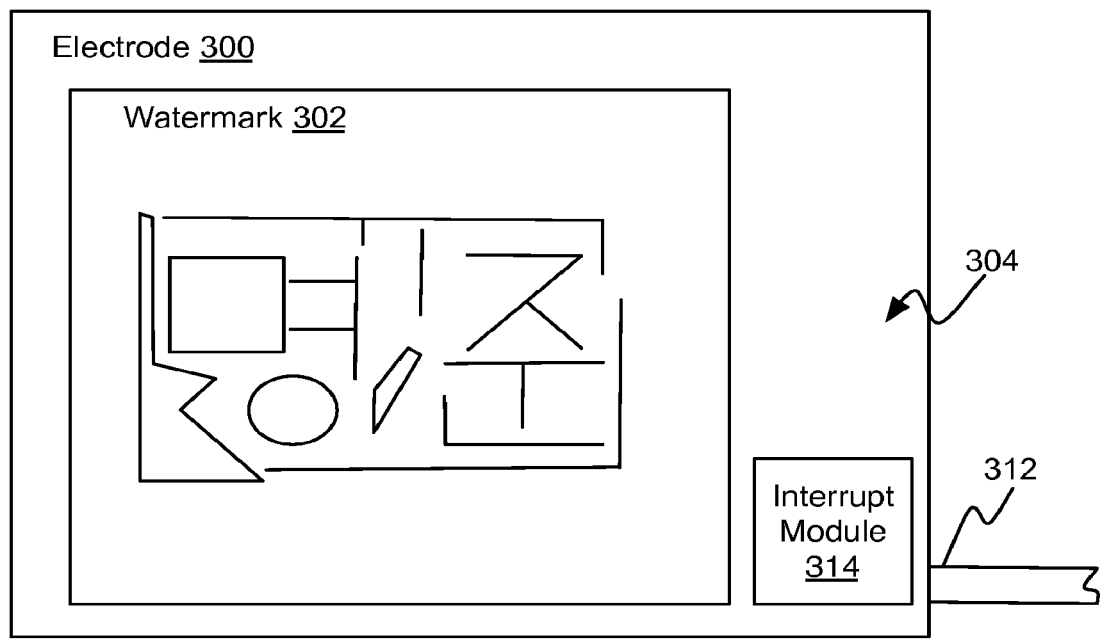
FIGS. 3a and 3b illustrate block diagrams of an electrode having communicative capabilities, in accordance with various embodiments.
Figure 3B:
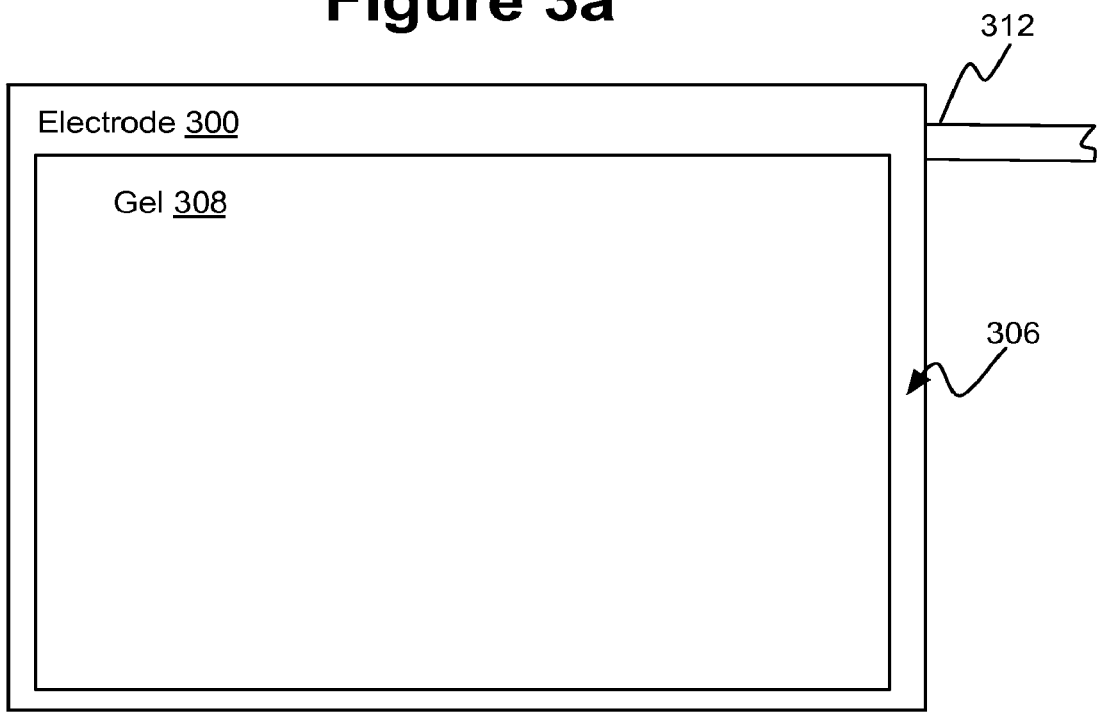

FIGS. 3a and 3b illustrate block diagrams of an electrode having communicative capabilities, in accordance with various embodiments. Shown in FIG. 3a is an electrode 300, which may be configured to be used with a defibrillator device 102 (e.g., an AED). The electrode 300 may have a watermark 302 integrated with the electrode 300 on a first surface 304 of the electrode 300.

In FIG. 3b, a second surface 306 of the electrode 300 may be shown. The second surface 306 may be substantially opposite the first surface 302 (shown in FIG. 3a), and a gel 308 may be disposed on the second surface 306. In both FIGS. 3a and 3b, a connector 312 may be shown electrically coupled to the electrode 300 and configured to electrically connect the electrode 300 to the defibrillator device 102. Additionally, in both FIGS. 3a and 3b, an electrical signal interrupt module 314 may be communicatively coupled to the connector 312 and the defibrillator device 102. As will be described in detail, the electrical interrupt module may be configured to interrupt an electrical signal from the defibrillator device 102 based, at least in part, on an interrupt signal from the defibrillator device 102.

In one example, the watermark 302 may comprise of an optical machine-readable watermark. In another example, the watermark 302 may comprise of an automatic identification and data capture (AIDC) watermark. In another example, the watermark 302 may comprise a universal product code (UPC). In another example, the watermark 302 may comprise a matrix type code. In another example, the watermark 302 may comprise a quick response (QR) code. In yet another example, the watermark 302 may comprise of a watermark capable of visually changing over time.

In the example of the watermark 302 capable of visually changing over time, the watermark 302 may comprise of a watermark having migrating ink. In yet another example of the watermark 302 capable of visually changing over time, the watermark 302 may comprise of visually changing paper.

In one example, the connector 312 may comprise of a quick release connector having a pull-tab device type. In yet another example, the quick release connector may comprise of a looped flange.

In one example, the electrical signal interrupt module 314 may comprise a residual-current device (RCD). An example of an RCD may comprise an automatic disconnection of supply (ADS) type device.

A non-limiting example of utilization of the electrode 300 may now be described. Briefly referring back to FIG. 1, the scenario may be similar to the one shown in FIG. 1. However, when the user turns on the defibrillator device 102, an audio and/or visual instruction may instruct the user to hold the electrode 300 in proximity to an image capture module included in the defibrillator device 102. The defibrillator device 102 may instruct the user that the defibrillator device 102 may capture an image of the watermark 302 on the first surface 304. In this example, the defibrillator device 102 may read the watermark 302 and determine a wide variety of information from the watermark such as, but not limited to the serial number and/or identification of the electrode 300, date of manufacture of the electrode 300, an expiration date of the electrode 300, an defibrillator device compatibility information (i.e., defibrillator device manufacturer compatibility with the electrode 300), electrical capabilities of the electrode 300, maximum recommended number of uses for the electrode 300, and so forth as previously described. Alternatively, the defibrillator device 102 may instruct the user to use a mobile device (not shown) to read the watermark 302 on the electrode 300. The mobile device may be a smart phone type device, which may be capable of reading the watermark 302 and retrieving various information (e.g., any information previously described or any combination thereof). For example, the smart phone may retrieve the information regarding the electrode 300 and/or the defibrillator device 102 via the Internet.

Referring back to the example of the defibrillator device 102 having the capabilities to read the watermark 302, if it is determined that the effectiveness of the electrode 300 may be questionable based, at least in part, on the information read from the watermark 302, the defibrillator device 102 may cause the electrical signal interrupt module 314 to interrupt substantially most of the electrical signals between the electrode 300 and the defibrillator device 102 via the connector 312 (e.g., voltage for the shock, while allowing electrical signals related to the heart 114 to continue being transmitted to the defibrillator device 102). If the defibrillator device 102 causes an interruption of substantially most of the electrical signal, the defibrillator device 102 may further instruct the user to connect alternate electrodes.

In the example of the watermark 302 configured to visually change over time, the watermark 302 may visually indicate that the electrode 300 has expired (e.g., the gel 308 and/or its adhesive properties may be outside a manufacturer limits). It should be reminded here that an electrode commonly has an expiration date as previously described.

Figure 4A:
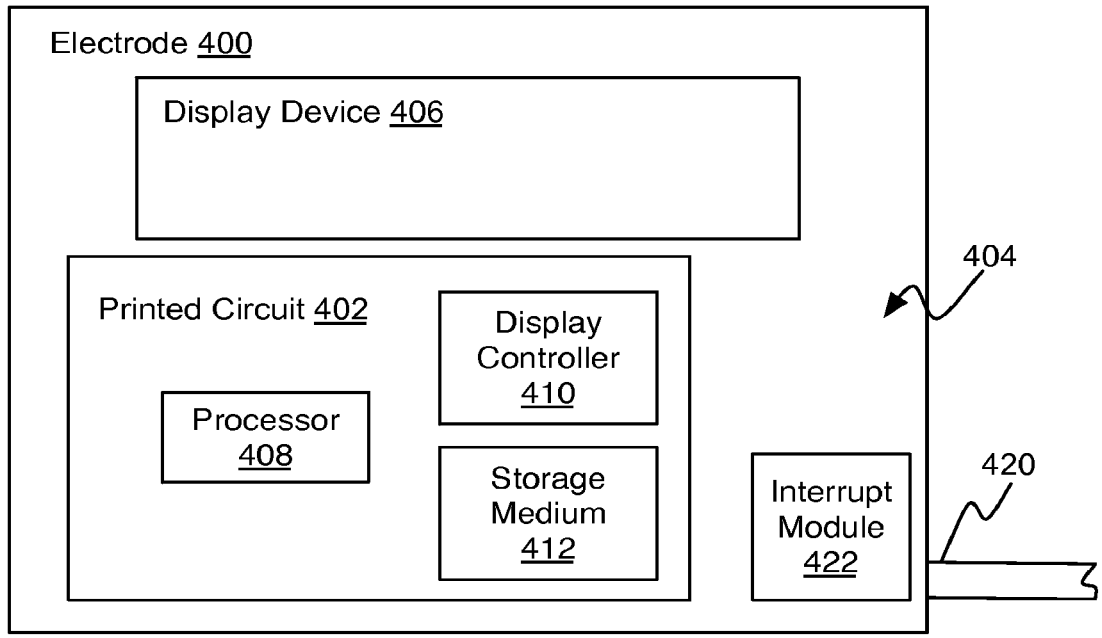
FIGS. 4a and 4b illustrate block diagrams of an electrode having communicative capabilities, in accordance with various embodiments.
Figure 4B:
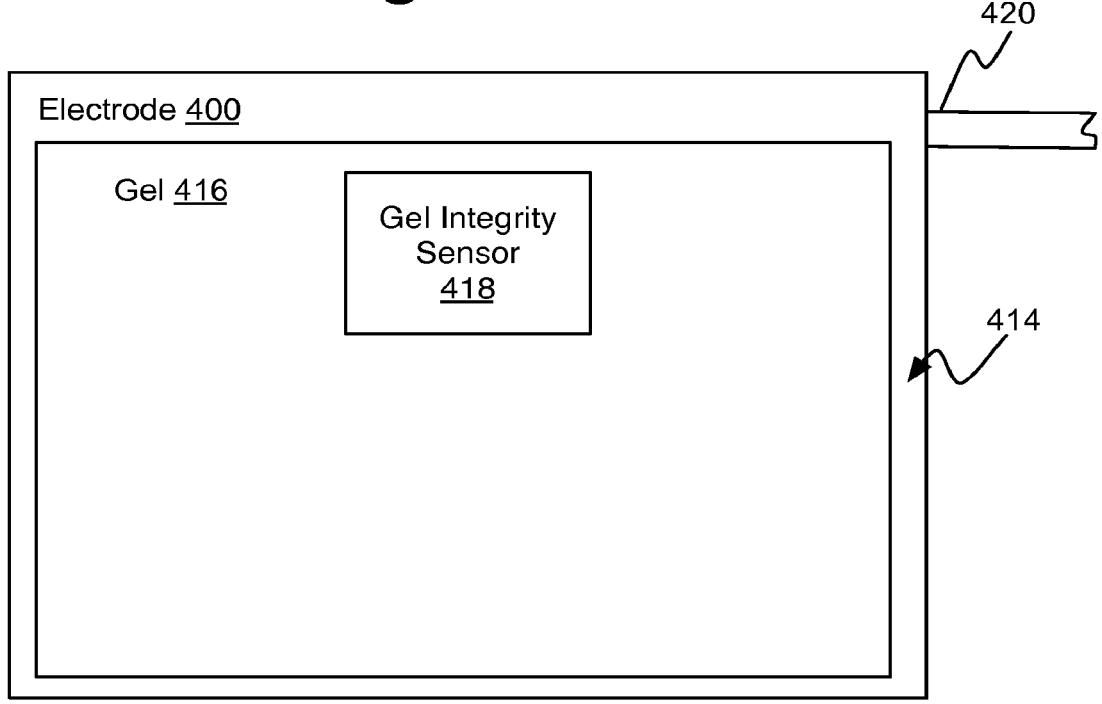

FIGS. 4a and 4b illustrate block diagrams of an electrode having communicative capabilities, in accordance with various embodiments. Shown in FIG. 4a, is an electrode 400, which may be configured to be used with a defibrillator device 102 (e.g., an AED). The electrode 400 may have a printed circuit 402 disposed on a first surface 404 of the electrode 400. The electrode 400 may additionally include a display device 406 disposed on the first surface 402. The display device 406 may be communicatively coupled to the printed circuit 402. The printed circuit 402 may include various functional blocks such as, but not limited to, a processor 408, a display controller 410, and a storage medium 412.

In FIG. 4b, a second surface 414 of the electrode 400 may be shown. The second surface 414 may be substantially opposite the first surface 404 (shown in FIG. 4a), and a gel 416 may be disposed on the second surface 414. Additionally, a gel integrity sensor 418 may be disposed in physical contact with the gel 416. The gel integrity sensor 418 may be communicatively coupled to the printed circuit 402. In both FIGS. 4a and 4b, a connector 420 may be shown electrically coupled to the electrode 400 and configured to electrically connect the electrode 400 to the defibrillator device 102. Shown in FIGS. 4a and 4b, an electrical signal interrupt module 422 may be communicatively coupled to the connector 420. The connector 420 may be configured to interrupt substantially most electrical signals between the electrode 400 and the defibrillator device 102 upon receiving an interrupt signal from the printed circuit 402 and/or from the defibrillator device 102. The electrode 400 shown in FIGS. 4a and 4b may facilitate various communicative capabilities for the electrode for use with the defibrillator device 102, in accordance with various embodiments of the disclosure.

In one example, the display device 406 may comprise of a liquid crystal display (LCD) type device. In another example, the gel 416 may comprise of at least one of a conductive gel or an adhesive gel for use with the electrode 400.

A non-limiting example of utilization of the electrode 400 may now be described. Referring back to FIG. 1, the first communicative apparatus 104 and the second communicative apparatus 106 may comprise of the electrode 400 described in FIGS. 4a and 4b. For this non-limiting example, references may be made to electrode 400 to describe the various functionalities of the first communicative apparatus 104 and the second communicative apparatus 106 (shown in FIG. 1). Continuing to refer to FIG. 1, a user (not shown) may have seen a person 112 experiencing some form of heart event such as, but not limited to, an arrhythmia event (e.g., VF). The user may have located and retrieved a defibrillator device 102 (e.g., an AED) from its holding location (e.g., an AED cabinet on a column and/or wall not shown). The user would open the defibrillator device package (not shown) and proceed to turn on the defibrillator device 102.

Referring now to FIGS. 4a and 4b, in one example, once the defibrillator device 102 is turned on, an audio instruction may instruct the user to connect the electrode 400 to the defibrillator device 102 via the connector 420. Once connected, printed circuit 402 and the display device 406 may receive power from the defibrillator device 102 via the connector 420. The processor 408 may read instructions stored in the storage medium 412 where, when executed, the display device 406 may display various information regarding the electrode 400. That is, the processor may execute instructions to manage the display device 400 via the display controller 410. In one example, the instructions from the storage medium 412 may include instructions that, when executed by the processor 408, causes the processor 408 to determine an integrity of the gel 416 on the second surface 414. The integrity of the gel 416 may be determined by data received from the gel integrity sensor 418 by the processor 408. The gel integrity sensor 418 may be capable of measuring the conductivity level of the gel 418. The processor 408 may receive the conductivity information from the gel integrity sensor 418. The processor 408 may determine if the received conductivity level is within predetermined level (e.g., impedance level) as may be stored in the storage medium 412.

In one example, if the processor 408 determines that the conductivity level of the gel 418 is outside a predetermined level, the processor 408 may cause the display device 406 to display a message that indicates to the user that the electrode may not be effective and that alternate electrodes should be used. In another example, the processor 408 may determine that the electrode 400 may not have been connected properly (e.g., the electrical signal between the electrode 400 and the defibrillator device 102 may not be clear). In this example situation, the processor 408 may cause the display device 406 to display a message that may indicate to that affect. That is, the processor 406 may cause the display device 406 to display any type of visual information to the user such as, but not limited to, conductivity level of the gel 416, serial number and/or identification of the electrode 400, date of manufacture of the electrode 400, an expiration date of the electrode 400, an defibrillator device compatibility information (i.e., a defibrillator device manufacturer compatibility with the electrode 400), number of cycles the electrode 400 has been subjected to, electrical capabilities of the electrode 400, maximum recommended number of uses for the electrode 400, identification of different devices to which the electrode 400 may have been previously connect, time the electrode 400 has been attached to a person, the person's electrical activity of the heart 114 over a period of time as detected by the defibrillator device 102 from the electrode 400 or electrocardiogram (i.e., ECG or EKG), and so forth. Some, all, or any combination of displayed information may be stored in the storage medium 412 and may be subsequently displayed at any time. For example, the ECG may be stored in the storage medium 412 and subsequently displayed at a medical facility for a medical personnel.

In one example, if the processor 408 determines that the conductivity level of the gel 418 is outside a predetermined level, the processor 408 may cause an interruption of substantially most of the electrical signals between the electrode 400 and the defibrillator device 102 via the connector 212 (e.g., voltage for the shock, while allowing electrical signals related to the heart 114 to continue being transmitted to the defibrillator device 102) by transmitting an electrical signal to the electrical signal interrupt module 422. In another example, the processor 408 may determine that the electrode 400 may not have been connected properly (e.g., the electrical signal between the electrode 400 and the defibrillator device 102 may not be clear). Here again, the processor 408 may cause an interruption of substantially most of the electrical signals between the electrode 400 and the defibrillator device 102 by transmitting an electrical signal to the electrical signal interrupt module 422. As in some previous examples, the processor 408 may store a wide variety of information in storage medium 412 such as, but not limited to, the determined conductivity level of the gel 416.

Figure 5:
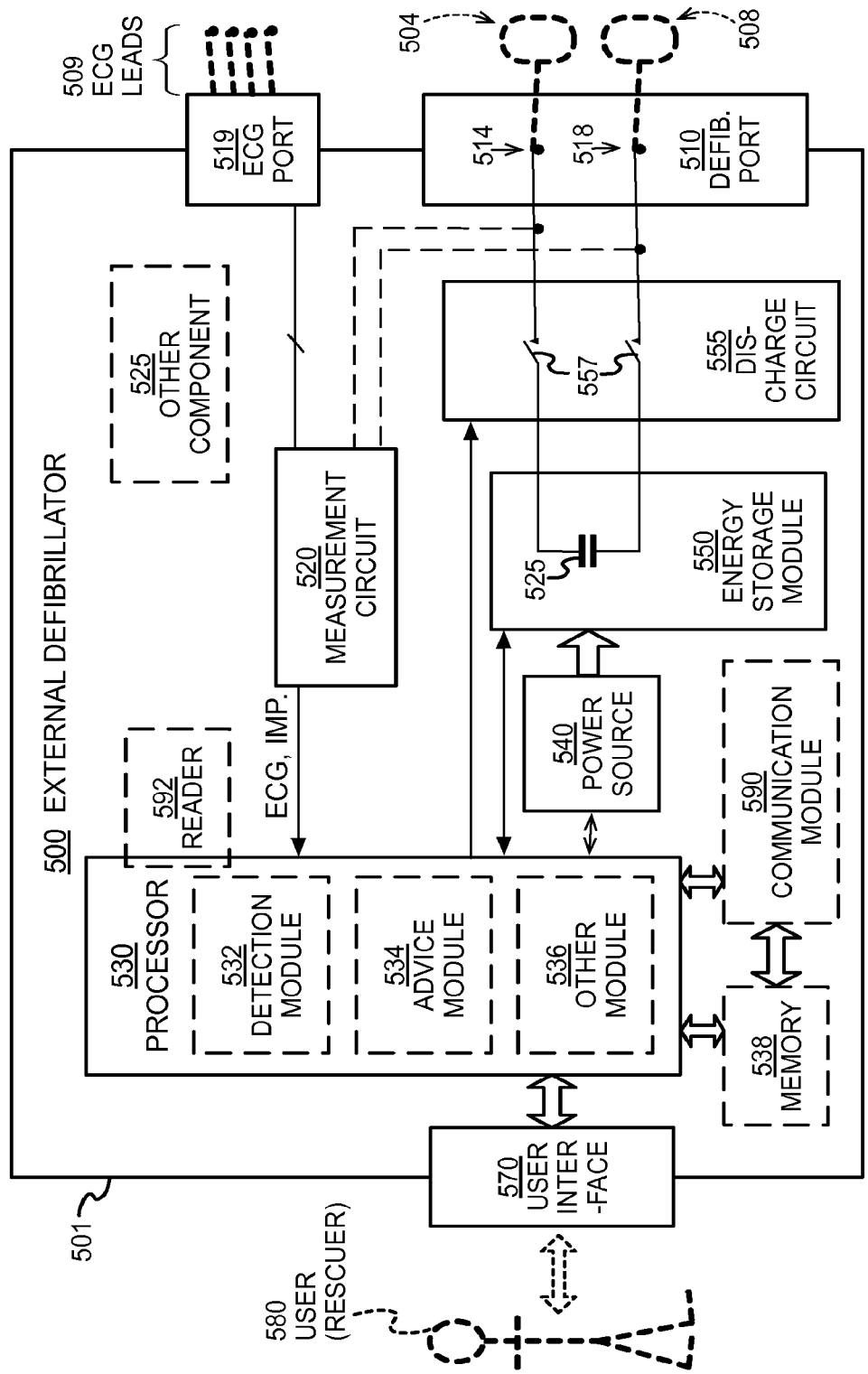
FIG. 5 is a block diagram illustrating components of an electrical device, which may be used and in accordance with various embodiments.

It should be appreciated that even though in FIGS. 2a-3b, the connectors 212, 312, and 420 may be shown as communicatively coupled to the electrodes 200, 300, and 400, the connectors 212, 312, and 420 may be a pluggable type communicative coupling. For example, FIG. 5 is a block diagram illustrating components of defibrillator device 500, which may be used with various embodiments. These components may be, for example, a defibrillator device 102 (shown in FIG. 1). Additionally, the components of FIG. 5. 3 may be provided in a housing 501, which may be known as casing 501.

The defibrillator device 500 may be intended for use by a user 580 (e.g., a rescuer). The defibrillator device 500 may typically include a defibrillation port 510, such as a socket in housing 501. The defibrillation port 510 may include nodes 514 and 518. One or more electrodes 504 and 508, which may be similar to electrodes 104, 106, 200, 300, and 400, may be plugged in to the defibrillation port 510, so as to make electrical contact with nodes 514 and 518, respectively. It may also be possible that the electrodes 504 and 508 may be connected continuously to the defibrillation port 510, etc. Either way, the defibrillation port 510 may be used for guiding via the electrodes 504 and 508 to the person 112 an electrical charge that may have been stored in the defibrillator device 500, as described herein. As previously described, some, any, all, or any combination thereof of the components/modules illustrated in FIGS. 2a-3b may be included substantially at or substantially near the defibrillator port 510 (e.g., at or near nodes 514 and/or 518). In other words, the described examples of FIGS. 2a-3b may be implemented on a connector at a substantially opposite end of an electrode.

If the defibrillator device 500 comprise of a defibrillator-monitor, as was described with reference to FIGS. 4a and 4b, the defibrillator device 500 may also have an ECG port 519 in the housing 501, for receiving ECG leads 509. The ECG leads 509 may facilitate sensing of an ECG signal (e.g., a 12-lead signal or from a different number of lead signals). Moreover, a defibrillator-monitor could have additional ports (not shown), and the other component 525 may be configured to filter the ECG signal (e.g., application of at least one filter to the signal to help facilitate removal of artifacts such as, but not limited to, chest compression due to chest compressions being delivered to the person 112).

The defibrillator 500 also may include a measurement circuit 520. The measurement circuit 520 may receive physiological signals from the ECG port 519, and also from other ports, if provided. The circuit 520 may render detected physiological signals and their corresponding information. The information may be in the form of data, or other signals, etc.

If the defibrillator 500 is configured as an AED type device, ECG port 519 may not be present. The measurement circuit 520 may obtain physiological signals through the nodes 514 and 518 instead, when the electrodes 504 and 508 are attached to the person 112, as previously described. In these cases, a person's ECG signal may be detected as a voltage difference between the electrodes 504 and 508. Additionally, the impedance between the electrodes 504 and 508 may detect, among other things, whether the electrodes 504 and 508 have been inadvertently disconnected from the person 112.

The defibrillator 500 may also include a processor 530. The processor 530 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 530 may include a number of modules. One example module may be a detection module 532, which may detect outputs from the measurement circuit 520. The detection module 532 may include a VF detector. Accordingly, the person's detected ECG may be utilized to help determine whether the person is experiencing VF.

In another example, advice module 534 may provide advice based, at least in part, on outputs of detection module 532. The advice module 534 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user and prompt them to do it. In other examples, the defibrillator device may execute the advice by administering the shock. If the advice is to administer CPR, the defibrillator 500 may further issue prompts for administrating CPR, and so forth.

The processor 530 may include additional modules, such as module 536 for various other functions. Additionally, if other component 525 is provided, it may be operated in part by processor 530, etc.

In an example, the defibrillator device 500 may include a memory 538, which may work together with the processor 530. The memory 538 may be implemented in a wide variety of manners. For example, the memory 538 may be implemented such as, but not limited to, nonvolatile memories (NVM), read-only memories (ROM), random access memories (RAM), and so forth or any combination thereof. The memory 538 may include programs for the processor 530, and so on. The programs may include operational programs executed by the processor 530 and may also include protocols and methodologies so that decisions may be made by advice module 534. Additionally, the memory 538 may store various prompts for the user 580, etc. Moreover, the memory 538 may store a wide variety of information (i.e., data) such as, but not limited to information regarding the person 112.

The defibrillator 500 may also include a power source 540. In order to facilitate portability of defibrillator device 500, the power source 540 may include a battery type device. A battery type device may be implemented as a battery pack, which may be rechargeable or not-rechargeable. At times, a combination of rechargeable and non-rechargeable battery packs may be utilized. Examples of power source 540 may include AC power override, where AC power may be available, and so on. In some examples, the processor 530 may control the power source 540.

Additionally, the defibrillator device 500 may include an energy storage module 550. The energy storage module 550 may be configured to store some electrical energy (e.g., when preparing for sudden discharge to administer a shock). The energy storage module 550 may be charged from the power source 540 to an appropriate level of energy, as may be controlled by the processor 530. In some implementations, the energy storage module 550 may include one or more capacitors 552, and the like.

The defibrillator 500 may include a discharge circuit 555. The discharge circuit 555 may be controlled to facilitate discharging of the energy stored in energy storage module 550 to the nodes 514 and 518, and also to electrodes 304 and 308. The discharge circuit 555 may include one or more switches 557. The one or more switches 557 may be configured in a number of manners such as, but not limited to, an H-bridge, and so forth.

The defibrillator device 500 may further include a user interface 570 for the user 580. The user interface 570 may be implemented in a variety of manners. For example, the user interface 570 may include a display screen capable of displaying what is detected and measured, provide visual feedback to the user 580 for their resuscitation attempts, and so forth. The user interface 570 may also include an audio output such as, but not limited to, a speaker to issue audio prompts, etc. The user interface 570 may additionally include various control devices such as, but not limited to, pushbuttons, keyboards, switches, track pads, and so forth. Additionally, the discharge circuit 555 may be controlled by the processor 530 or directly by the user 580 via the user interface 570, and so forth.

Additionally, the defibrillator device 500 may include other components. For example, a communication module 590 may be provided for communicating with other machines and/or the electrodes 404 and 408, as previously described. Such communication may be performed wirelessly, or via wire, or by infrared communication, near field communication (NFC), Bluetooth, WiFi, and so forth. Accordingly, information may be communicated, such as person data, incident information, therapy attempted, CPR performance, ECG information, and so forth.

A feature of a defibrillator device may be CPR related prompting. CPR prompts may be issued to the user 580 visually or by audio facilitating assistance in the administration of CPR by the user 580. Examples may be found in U.S. Pat. Nos. 6,334,070 and 6,356,785.

Figure 6:
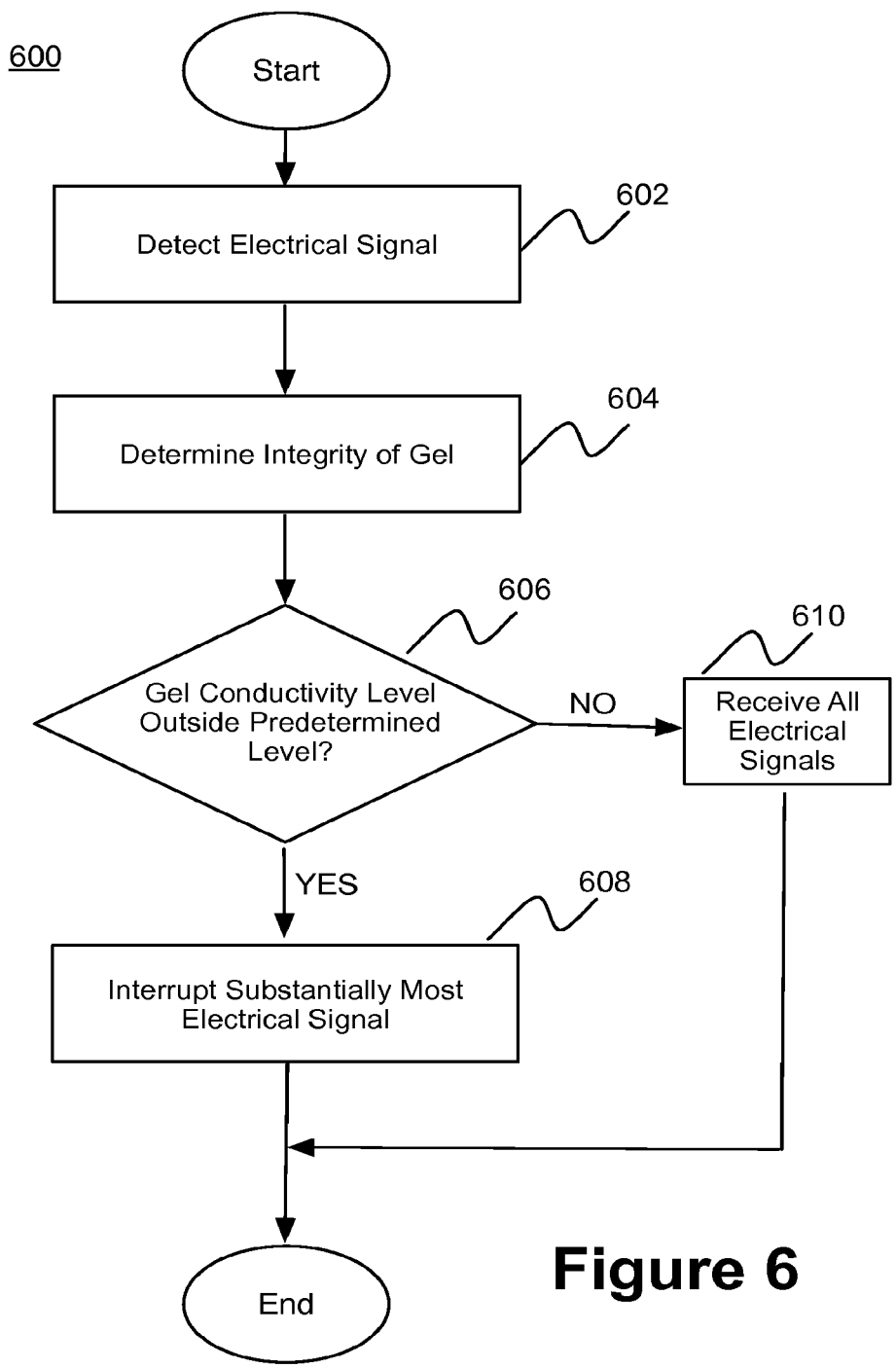
FIG. 6 illustrates an operational flow for an electrical device electrode having various communicative capabilities, arranged in accordance with at least some embodiments described herein.

FIG. 6 illustrates an operational flow for a defibrillator electrode having various communicative capabilities, arranged in accordance with at least some embodiments described herein. In some portions of the description, illustrative implementations of the method are described with reference to the elements of electrodes depicted in FIGS. 1, 2a, 2b, 4a, and 4b. However, the described embodiments are not limited to these depictions. More specifically, some elements depicted in FIGS. 2a, 2b, 4a, and 4c may be omitted from some implementations of the methods details herein. Furthermore, other elements not depicted in FIGS. 1, 2a, 2b, 4a, and 4b may be used to implement example methods detailed herein.

Additionally, FIG. 6 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 600 may be employed as part of a defibrillator electrode having various communicative capabilities. Beginning at block 602 ("Detect Electrical Signal"), the electrode 200 (shown in FIGS. 1, 2a, and 2b) may detect a wireless signal. As described, the electrode 200 may include the thin film circuit 202, where the thin film circuit 202 may be configured to be an RFID circuit.

Continuing from block 602 to 604 ("Determine Integrity of Gel"), the electrode 200 may determine the integrity level of the gel 208 via the gel integrity sensor 210. Integrity of the gel 208 may include a wide variety of information regarding the gel 208 such as, but not limited to, conductance, impedance, capacitance, humidity, temperature cycles, proper storage, expiration, and so forth, as previously described.

Continuing from block 604 to decision diamond 606 ("Gel Conductivity Level Outside Predetermined Level?"), the electrode may compare the determined integrity level of the gel 208 (e.g., conductivity level of the gel) with a predetermined range. As mentioned, conductivity may be but one example of information regarding the gel 208. Accordingly, in at least this respect, the claimed subject matter is not limited in scope.

In one example, if it is determined that the conductivity level of the gel is outside the predetermined range, the electrode 200 may cause an interruption of substantially most of the electrical signals between the electrode 200 and the defibrillator device 102 via the electrical interrupt signal module 216, at block 608 ("Interrupt Substantially Most Electrical Signal"). However, if it is determined that conductivity level of the gel is within the predetermined range, the electrode 200 may receive substantially all of the electrical signals from the defibrillator device 102 including an electrical shock 116 (shown in FIG. 1) if appropriate, at block 610 ("Receive All Electrical Signals").

In general, the operational flow described with respect to FIG. 6 and elsewhere herein may be implemented as a computer program product, executable on any suitable computing system, or the like. For example, a computer program product for facilitating a defibrillator electrode having communicative capabilities may be provided. Example computer program products may be described with respect to FIG. 7 and elsewhere herein.

FIG. 7 illustrates an example computer program product 700, arranged in accordance with at least some embodiments described herein. Computer program product 700 may include machine readable non-transitory medium having stored therein instructions that, when executed, cause the machine to utilize a defibrillator electrode having communicative capabilities, according to the processes and methods discussed herein. Computer program product 700 may include a signal bearing medium 702. Signal bearing medium 702 may include one or more machine-readable instructions 704 which, when executed by one or more processors, may operatively enable a computing device to provide the functionality described herein. In various examples, the devices discussed herein may use some or all of the machine-readable instructions.

In some examples, the machine readable instructions 704 may include detecting an electrical signal. In some examples, the machine readable instructions 704 may include determining an integrity level of a gel. In some examples, the machine readable instructions 704 may include determining if the conductivity level of the gel within a predetermined range. Here again, it should be appreciated that conductivity of the gel 208 may include a wide variety of information regarding the gel 208 such as, but not limited to, conductance, impedance, capacitance, humidity, temperature cycles, proper storage, expiration, and so forth, as previously described, and accordingly, in at least this respect, the claimed subject matter is not limited in scope. In some examples, the machine readable instructions 704 may include interrupting substantially most of the electrical signals between the electrode and the defibrillator device.

In some implementations, signal bearing medium 702 may encompass a computer-readable medium 706, such as, but not limited to, a hard disk drive, a Compact Disc (CD), a Digital Versatile Disk (DVD), a Universal Serial Bus (USB) drive, a digital tape, memory, etc. In some implementations, the signal bearing medium 702 may encompass a recordable medium 708, such as, but not limited to, memory, read/write (R/W) CDs, R/W DVDs, etc. In some implementations, the signal bearing medium 702 may encompass a communications medium 710, such as, but not limited to, a digital and/or an analog communication medium (e.g., a fiber optic cable, a waveguide, a wired communication link, a wireless communication link, etc.). In some examples, the signal bearing medium 702 may encompass a machine readable non-transitory medium.

In general, the methods described with respect to FIG. 6 and elsewhere herein may be implemented in any suitable computing system. Example systems may be described with respect to FIG. 8 and elsewhere herein. In general, the system may be configured to facilitate utilization of a defibrillator electrode having communicative capabilities.

Figure 8:
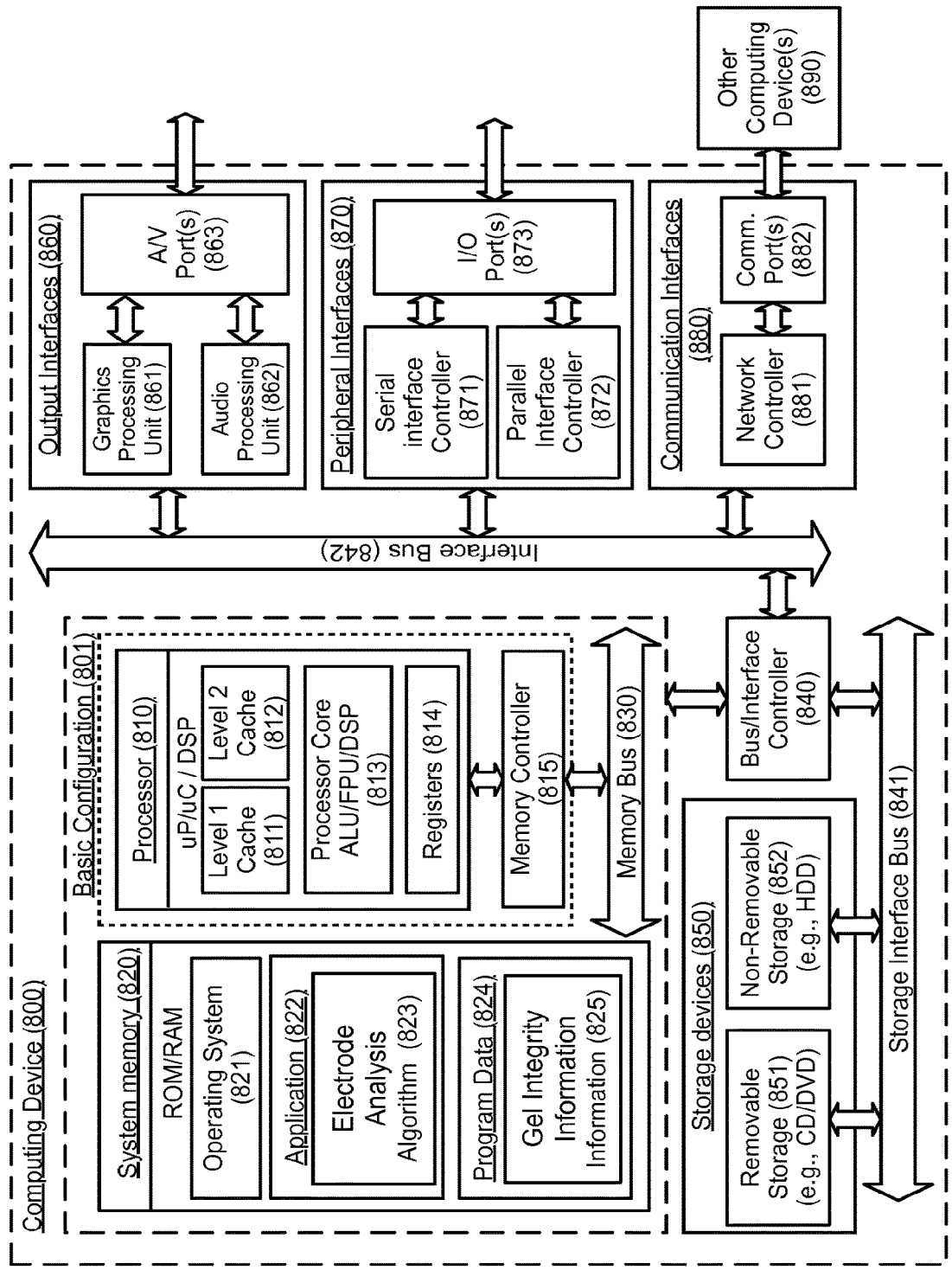
FIG. 8 is a block diagram illustrating an example computing device 800, such as might be embodied by a person skilled in the art, which is arranged in accordance with at least some embodiments of the present disclosure.

FIG. 8 is a block diagram illustrating an example computing device 800, such as might be embodied by a person skilled in the art, which is arranged in accordance with at least some embodiments of the present disclosure. In one example configuration 801, computing device 800 may include one or more processors 810 and system memory 820. A memory bus 830 may be used for communicating between the processor 810 and the system memory 820.

Depending on the desired configuration, processor 810 may be of any type including but not limited to a microprocessor (µP), a microcontroller (µC), a digital signal processor (DSP), or any combination thereof. Processor 810 may include one or more levels of caching, such as a level one cache 811 and a level two cache 812, a processor core 813, and registers 814. The processor core 813 may include an arithmetic logic unit (ALU), a floating point unit (FPU), a digital signal processing core (DSP Core), or any combination thereof. A memory controller 815 may also be used with the processor 810, or in some implementations the memory controller 815 may be an internal part of the processor 810.

Depending on the desired configuration, the system memory 820 may be of any type including but not limited to volatile memory (such as RAM), non-volatile memory (such as ROM, flash memory, etc.) or any combination thereof. System memory 820 may include an operating system 821, one or more applications 822, and program data 824. Application 822 may include electrode analysis algorithm 823 that is arranged to perform the functions as described herein including the functional blocks and/or actions described. Program Data 824 may include, among a wide variety of information described, gel integrity information 825 for use with electrode analysis algorithm 823. In some example embodiments, application 822 may be arranged to operate with program data 824 on an operating system 821 such that implementations of defibrillator electrodes having communicative capabilities may be provided as described herein. For example, apparatus described in the present disclosure may comprise all or a portion of computing device 800 and be capable of performing all or a portion of application 822 such that implementations of defibrillator electrodes having communicative capabilities may be provided as described herein. This described basic configuration is illustrated in FIG. 8 by those components within dashed line 801.

Computing device 800 may have additional features or functionality, and additional interfaces to facilitate communications between the basic configuration 801 and any required devices and interfaces. For example, a bus/interface controller 840 may be used to facilitate communications between the basic configuration 801 and one or more data storage devices 850 via a storage interface bus 841. The data storage devices 850 may be removable storage devices 851, non-removable storage devices 852, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 820, removable storage 851 and non-removable storage 852 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of device 900.

Computing device 800 may also include an interface bus 842 for facilitating communication from various interface devices (e.g., output interfaces, peripheral interfaces, and communication interfaces) to the basic configuration 801 via the bus/interface controller 840. Example output interfaces 860 may include a graphics processing unit 861 and an audio processing unit 862, which may be configured to communicate to various external devices such as a display or speakers via one or more A/V ports 863. Example peripheral interfaces 860 may include a serial interface controller 871 or a parallel interface controller 872, which may be configured to communicate with external devices such as input devices (e.g., keyboard, mouse, pen, voice input device, touch input device, etc.) or other peripheral devices (e.g., printer, scanner, etc.) via one or more I/O ports 873. An example communication interface 880 includes a network controller 881, which may be arranged to facilitate communications with one or more other computing devices 890 over a network communication via one or more communication ports 882. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 800 may be implemented as a portion of a small-form factor portable (or mobile) electronic device such as a cell phone, a personal data assistant (PDA), a tablet type device, a personal media player device, a wireless web-watch device, a personal headset device, an application specific device, or a hybrid device that includes any of the above functions. Computing device 800 may also be implemented as a personal computer including both laptop computer and non-laptop computer configurations. In addition, computing device 800 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussion utilizing terms such as "processing," "computing," "calculating," "determining" or the like refer to actions or processes of a computing device that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as those employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon that, when executed by a computing device such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skilled in the art in light of this disclosure. In addition, those skilled in the art will appreciate that the mechanisms of the subject matter described herein are capable of being distributed as a product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A therapy electrode, comprising:
   a pad having a first surface and a second surface opposite the first surface;
   a circuit disposed on the first surface of the pad;
   gel disposed on the second surface of the pad; and
   a gel integrity sensor coupled to the circuit and disposed on the second surface of the pad, the gel integrity sensor configured to:
   sense a characteristic associated with an integrity of the gel, and
   send, to the circuit, information indicative of the sensed characteristic associated with the integrity of the gel, and
   the circuit configured to determine, based at least in part on the information, an integrity level of the gel.

2. The therapy electrode of claim 1, wherein the circuit comprises a processor configured to execute instructions that cause the processor to determine the integrity level of the gel based at least in part on the information.

3. The therapy electrode of claim 1, wherein the circuit comprises a Radio Frequency Identification (RFID) tag.

4. The therapy electrode of claim 3, wherein the RFID tag comprises a passive tag.

5. The therapy electrode of claim 1, wherein the circuit comprises a communication module configured to receive data.

6. The therapy electrode of claim 1, wherein the gel comprises a conductive gel.

7. The therapy electrode of claim 1, wherein the gel integrity sensor comprises a conductivity sensor configured to sense a conductivity level of the gel and wherein the information is indicative of the sensed conductivity level of the gel.

8. The therapy electrode of claim 1, wherein the gel integrity sensor comprises a humidity and temperature sensor configured to sense a moisture content and temperature of the gel and wherein the information is indicative of the sensed moisture content and temperature of the gel.

9. The therapy electrode of claim 5, wherein the communication module is further configured to receive an instruction to cause the circuit to evaluate the information indicative of the sensed characteristic associated with the integrity of the gel.

10. The therapy electrode of claim 1, wherein the circuit is further configured to evaluate the information and determine if a value associated with the integrity level of the gel is within a predetermined range.

11. The therapy electrode of claim 1, wherein the therapy electrode is further configured to be coupled to a medical device, and wherein the circuit is further configured to cause, based at least in part on the integrity level of the gel, an interruption of first electrical signals to prevent an electrical shock from being delivered via the therapy electrode while allowing second electrical signals to be transmitted from the therapy electrode to the medical device.

12. The therapy electrode of claim 11, wherein the circuit is further configured to output a user instruction based at least in part on the interruption of the first electrical signals.

13. The therapy electrode of claim 1, further comprising a memory coupled to the circuit, the memory configured to store the information indicative of the sensed characteristic associated with the integrity of the gel.

14. The therapy electrode of claim 1, wherein the sensed characteristic associated with the integrity of the gel is one of a conductance of the gel, an impedance of the gel, a capacitance of the gel, a moisture content of the gel, a temperature cycle of the gel, and an expiration date of the gel.

15. The therapy electrode of claim 1, wherein the gel integrity sensor comprises:
    a conductivity sensor configured to sense a conductivity of the gel and to send the information indicative of the sensed conductivity.

16. The therapy electrode of claim 1, wherein the gel integrity sensor comprises a humidity and temperature sensor configured to:
sense a moisture content and temperature of the gel, and
send the information indicative of the sensed moisture content and temperature to which the therapy electrode has been subjected prior to a coupling of the therapy electrode to a medical device.

17. The therapy electrode of claim 3, wherein the RFID tag comprises an active tag.

18. The therapy electrode of claim 3, wherein the RFID tag comprises a battery-assisted passive tag.

19. The therapy electrode of claim 1, wherein the circuit comprises a communication module configured to transmit data.

20. The therapy electrode of claim 1, wherein the gel comprises an adhesive gel.

21. The therapy electrode of claim 5, wherein the communication module is further configured to receive an instruction to cause the circuit to determine if a value associated with the integrity level of the gel is within a predetermined range.

22. The therapy electrode of claim 1, further comprising a memory coupled to the gel integrity sensor, the memory configured to store the information indicative of the sensed characteristic associated with the integrity of the gel.

23. The therapy electrode of claim 1, wherein the gel integrity sensor comprises a humidity and temperature sensor configured to sense a moisture content and a temperature of the gel and to send the information indicative of the sensed moisture content and temperature.

24. A therapy electrode, comprising:
a pad having a first surface and a second surface opposite the first surface;
a circuit disposed on the first surface of the pad, the circuit having a processor;
gel disposed on the second surface of the pad; and
a gel integrity sensor coupled to the circuit and disposed on the second surface of the pad, the gel integrity sensor configured to:
sense a characteristic associated with an integrity of the gel, and
send, to the circuit, information indicative of the sensed characteristic associated with the integrity of the gel, and
the processor configured to process the information to determine a value associated with an integrity level of the gel.

25. The therapy electrode of claim 24, wherein the processor is further configured to cause, based at least in part on the value, an interruption of first electrical signals to prevent an electrical shock from being delivered via the therapy electrode while allowing second electrical signals to be transmitted from the therapy electrode to a medical device that is coupled to the therapy electrode.

26. The therapy electrode of claim 25, wherein causing the interruption based at least in part on the value comprises:
determining, by the processor, that the value is not within a predetermined range; and
causing the interruption based at least in part on determining that the value is not within the predetermined range.

27. An electrode configured to deliver an electrical shock, the electrode comprising:
a pad having a first surface and a second surface opposite the first surface;
a circuit disposed on the first surface of the pad;
gel disposed on the second surface of the pad; and
a gel integrity sensor coupled to the circuit and disposed on the second surface of the pad, the gel integrity sensor configured to:
sense a characteristic associated with an integrity of the gel, and
send, to the circuit, information indicative of the sensed characteristic associated with the integrity of the gel, and
the circuit configured to determine, based at least in part on the information, an integrity level of the gel.

28. The electrode of claim 27, wherein the circuit is further configured to cause, based at least in part on the integrity level of the gel, an interruption of first electrical signals to prevent the electrical shock from being delivered via the electrode while allowing second electrical signals to be transmitted from the electrode to a medical device that is coupled to the electrode.

29. The electrode of claim 28, wherein causing the interruption based at least in part on the integrity level of the gel comprises:
determining, by the circuit, that a value associated with the integrity level of the gel is not within a predetermined range; and
causing the interruption based at least in part on determining that the value is not within the predetermined range.

30. The electrode of claim 28, wherein the medical device comprises a defibrillator.

* * * * *